United States Patent
Sasai et al.

(10) Patent No.: US 7,351,835 B2
(45) Date of Patent: Apr. 1, 2008

(54) ORGANIC MOLECULAR CATAYLST HAVING BINAPHTHOL SKELETON AND PROCESSES FOR PRODUCING THE SAME AND APPLICATION THEREOF

(75) Inventors: Hiroaki Sasai, Osaka (JP); Shinobu Takizawa, Osaka (JP); Katsuya Matsui, Osaka (JP)

(73) Assignee: Meiji Seika Kaisha Ltd., Tokyo (JP)

( * ) Notice: Subject to any disclaimer, the term of this patent is extended or adjusted under 35 U.S.C. 154(b) by 418 days.

(21) Appl. No.: 11/075,859

(22) Filed: Mar. 10, 2005

(65) Prior Publication Data

US 2006/0009646 A1   Jan. 12, 2006

(30) Foreign Application Priority Data

Jul. 12, 2004  (JP)  .......................... P.2004-204183

(51) Int. Cl.
| C07D 213/74 | (2006.01) |
| C07B 53/00 | (2006.01) |
| C07C 257/18 | (2006.01) |
| C07D 233/88 | (2006.01) |
| C07F 9/50 | (2006.01) |

(52) U.S. Cl. .................... 546/312; 548/346.1; 564/247; 568/13

(58) Field of Classification Search ................. 546/312
See application file for complete search history.

(56) References Cited

FOREIGN PATENT DOCUMENTS

JP         11-035562         2/1999

OTHER PUBLICATIONS

Matsui et al., Journal of the American Chemical Society, 127(11), 3680-3681, Mar. 1, 2005.*
Matsui et al., Chemical Abstracts, 142:410938, 2005.*
English Language Abstract of JP 11-35562.
Matsui K., Takizawa S., Sasai H. "Development of Novel Multifunctional Catalyst for Enantioselective aza-Morita-Baylis-Hillman Reaction" ISIR, Osaka University, Abstracts of the 84th (Spring) Annual Meeting of the Chemical Society of Japan, Mar. 11, 2004, 4 F1-26, p. 853, accompanied by an unverified English language translation of relevant parts thereof.
Arai M., et al. "A New Asymmetric Wacker-Type Cyclicization and Tandem Cyclization Promoted by Pd(II)-Spiro Bis (isoxazoline) Catalyst" J. Am. Chem. Soc., 2001, 123, 2907-2908.
Arai T., et al. "" Catalyst Analogue": A Concept for Constructing Multicomponent Asymmetric Catalysts (MAC) Using a Polymer Support " Angew. Chem. Int. Ed., 2003, 42, 2144-2147.
Shi M., Xu Y.-M. "Lewis Base Effects in the Baylis-Hillman Reaction of Imines with Cyclohex-2-en-1-one and Cyclopent-2-en-1-one" Chem. Commun., 2001, 1876-1877.
Shi M., Xu Y.-M. "Lewis Base Effects in the Baylis-Hillman Reaction of Imines with Methyl Vinyl Ketone" Eur. J. Org. Chem., 2002, 696-701.
Shi M., Xu Y.-M. "Catalytic Asymmetric Baylis-Hillman Reaction of Imines with Methyl Vinyl Ketone and Methyl Acrylate", Angew. Chem. Int. Ed., 2002, 41, 4507-4510.
Shi M., Chen L.-H. "Chiral Phosphine Lewis Base Catalyzed Asymmetric aza- Baylis-Hillman Reaction of N-sulfonated Imines with Methyl Vinyl Ketone and Phenyl Acrylate" Chem. Commun., 2003, 1310-1311.
Li C.-J., et al. "Synthesis of a Bis-(Binaphthol)" Tetrahedron Letters, 1996, 37, 4459-4462.
Krishnamurthy S. "A Highly Efficient and General N-Monomethylation of Functionalized Primary Amines via Formylation—Borane:Methyl Sulfide Reduction" Tetrahedron Letters, 1982, 23, 3315-3318.
Vogl E.M., et al. "Linking BINOL: $C_2$-Symmetric Ligands for Investigations on Asymmetric Catalysis", Tetrahedron Letters, 1998, 39, 7917-7920.

* cited by examiner

*Primary Examiner*—Fiona T Powers
(74) *Attorney, Agent, or Firm*—Greenblum & Bernstein, P.L.C.

(57) ABSTRACT

A novel organic molecular catalysts represented by the following formula (1) or (2):

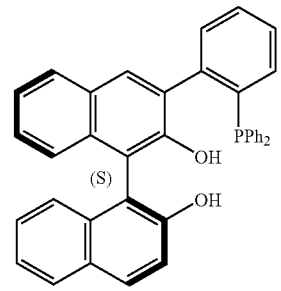

(1)

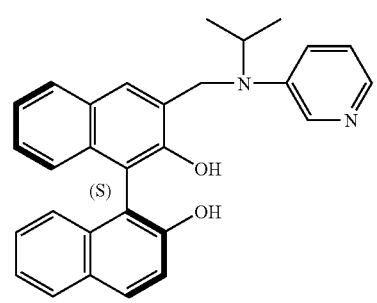

(2)

and a method for carrying out asymmetric reactions/asymmetric synthesis using these organic molecular catalysts.

4 Claims, No Drawings

ORGANIC MOLECULAR CATAYLST HAVING BINAPHTHOL SKELETON AND PROCESSES FOR PRODUCING THE SAME AND APPLICATION THEREOF

FIELD OF THE INVENTION

The present invention relates to the molecular design of a novel organic molecular catalyst having a binaphthol skeleton and the development of a method for producing the same, and an application thereof. More specifically, according to the present invention, an organic molecular catalyst which has been unknown are produced with known compounds as starting materials and useful asymmetric reactions are achieved using the resulting organic molecular catalysts. Therefore, the present invention provides a technology for efficiently producing useful compounds per se, e.g., pharmaceuticals, pesticides, veterinary medicines, functional molecules, and new material compounds, or important synthetic intermediates for producing useful compounds.

BACKGROUND OF THE INVENTION

The novel and useful present invention is summarized by two points that an excellent organic molecular catalyst which has been unknown is found and a certain asymmetric reactions which have been difficult to practically apply is efficiently realized using the organic molecular catalysts. The following will describe conventional technologies with regard to the respective points.

Compounds useful per se, e.g., pharmaceuticals, pesticides, veterinary medicines, functional molecules, and new material compounds, frequently contain asymmetric carbons and the efficient construction thereof belongs a category of problem which is most important and requires the highest production technique among recent problems in synthetic organic chemistry. As one of methods for efficiently constructing the asymmetric carbons during processes for producing the useful compounds per se, it is general to use asymmetric reactions. For the ultimate purpose of enhancing the efficiency as far as possible, a large number of organometallic catalysts have been recently molecularly designed and produced, and excellent usefulness thereof has been proved as described in *J. Am. Chem. Soc.*, 123, 2907-2908, 2001 and *Angew. Chem. Int. Ed.*, 42, 2144-2147, 2003. However, it cannot be said that the asymmetric reactions using the organometallic catalysts contain no problem. Namely, in the case when a step of using an organometallic catalyst is incorporated into the production of a final product or an intermediate, a minute amount of the metal remains in the final product and the complete elimination of the metal sometimes heightens the technical hurdle of production and purification of the product. Moreover, in the case when an asymmetric reaction is repeatedly carried out using an organometallic catalyst, it is sometimes observed that chemical yields or asymmetric yields decrease while the reaction is repeated. The above are problems in the application of organometallic catalysts to asymmetric reactions.

The following will describe the technologies for efficiently production of useful compounds per se, e.g., pharmaceuticals, pesticides, veterinary medicines, functional molecules, and new material compounds, or important synthetic intermediates for producing useful compounds. As the technologies, various asymmetric reactions have been reported, and recently a novel carbon-carbon bond-forming reaction wherein a substrate containing a nitrogen atom is involved as described in *Chem. Commun.*, 2001, 1876-1877 and *Eur. J. Org. Chem.*, 2002, 696-701. The reaction initially called "the Baylis-Hillman reaction of imine" at the time when it was found was at first not necessarily said to be as an excellent asymmetric reaction. However, thereafter, an asymmetric reaction has been achieved using an organic molecular catalyst derived from a natural product having asymmetry. Currently, production examples wherein asymmetric yields of 90% or more at maximum are realized by Shi et. al have been reported as described in *Angew. Chem. Int. Ed.*, 41, 4507-4510, 2002 and *Chem. Commun.*, 2003, 1310-1311 and thus the "aza-Baylis-Hillman reaction" as an asymmetric reaction has been acknowledged.

However, the asymmetric yields in the aza-Baylis-Hillman reaction have been achieved using organic molecular catalysts derived from natural products and the reaction contains not necessarily no problem as a technology for producing useful compounds per se, e.g., pharmaceuticals, pesticides, veterinary medicines, functional molecules, and new material compounds, or important synthetic intermediates for producing useful compounds. Namely, for the efficient production of useful compounds or important synthetic intermediates for producing the same, it is required a technology capable of freely constructing an asymmetric carbon which has a necessary stereochemistry, in other words, an efficient method capable of constructing any asymmetric center. As the most recent example of asymmetric reactions in this field, an asymmetric aza-Baylis-Hillman reaction using an organic molecular catalyst which has a binaphthyl skeleton has been reported by Shi et al. as described in *Chem. Commun.*, 2003, 1310-1311. However, any efficient application example capable of simultaneously realizing a high asymmetric yield of 90% or more and a practical chemical yield of 90% or more has not been known in the above reaction. Problems of the use of the aza-Baylis-Hillman reaction at the industrial construction of an asymmetric carbon are described above.

SUMMARY OF THE INVENTION

In the present invention, it is necessary to develop a novel organic molecular catalyst containing no organic metal. Furthermore, an object of the present invention is to provide a novel method for realizing industrially useful asymmetric reactions including the aza-Baylis-Hillman reaction as one example. Namely, the organic molecular catalyst to be provided by the present invention should be novel in the chemical structure and also should realize simultaneously high asymmetric yields and practical chemical yields which has not been reported in useful carbon-carbon bond-forming reactions including the aza-Baylis-Hillman reaction as one example. Furthermore, with regard to the stereochemistry of the asymmetric carbon to be constructed, it is required to enable construction of any stereochemistry based on the asymmetry of the organic molecular catalyst used.

As a result of extensive studies in synthetic chemistry for responding to the above expectation, the inventors of the present invention have found the method wherein a novel organic molecular catalyst which has a binaphthol skeleton, which are designed and synthesized by the inventors of the present invention, can simultaneously realize high asymmetric yields and practical chemical yields which has not reported in useful carbon-carbon bond-forming reactions including the aza-Baylis-Hillman reaction as one example. Thus, they have accomplished the present invention. Only a small number of examples wherein high asymmetric yields are achieved in the aza-Baylis-Hillman reaction using organic molecular catalysts derived from natural products have been known, and it has not been known a fact that a high asymmetric yield of 90% or more and a practical chemical yield of 90% or more are simultaneously achieved in the aza-Baylis-Hillman reaction using an organic molecular catalyst independent of any natural product, i.e., an organic molecular catalyst capable of constructing any asymmetry.

DETAILED DESCRIPTION OF THE INVENTION

Namely, the present invention provides:

(1) A compound represented by the following formula (I) or (II):

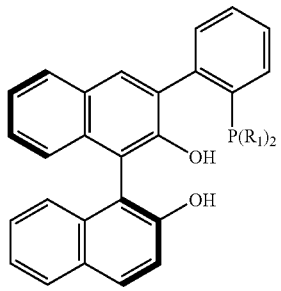
(I)

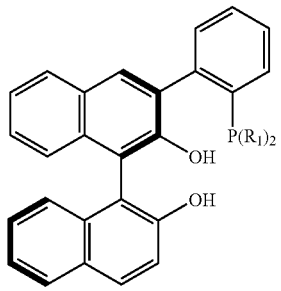
(II)

wherein $R_1$ represents a phenyl group which may be substituted by a lower alkyl group or a halogen atom.

(2) A compound represented by the following formula (III) or (IV):

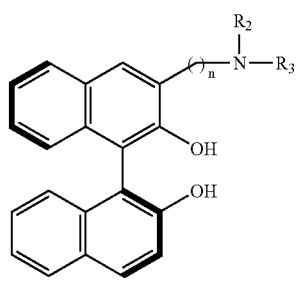
(III)

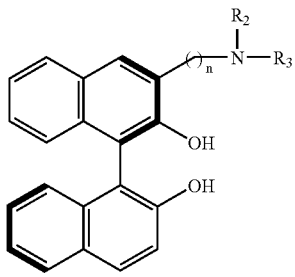
(IV)

wherein n represents an integer of 1 to 6, $R_2$ represents a hydrogen atom, a linear or branched alkyl group having 1 to 6 carbon atoms, a linear or branched alkenyl group having 2 to 6 carbon atoms, or an aralkyl group having 7 or 8 carbon atoms, $R_3$ represents a 2-pyridyl group which may be substituted by a lower alkyl group or a halogen atom, a 3-pyridyl group which may be substituted by a lower alkyl group or a halogen atom, or a 4-pyridyl group which may be substituted by a lower alkyl group or a halogen atom, or a salt thereof.

(3) A compound represented by the following formula (V) or (VI):

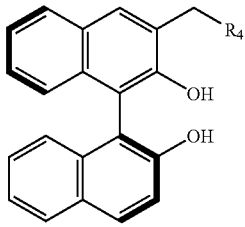
(V)

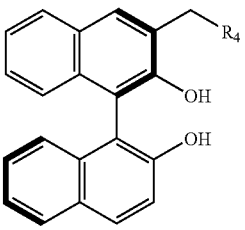
(VI)

wherein $R_4$ represents 2-imidazolyl group or 4-imidazolyl group, or a salt thereof.

(4) A compound represented by the following formula (VII) or (VIII):

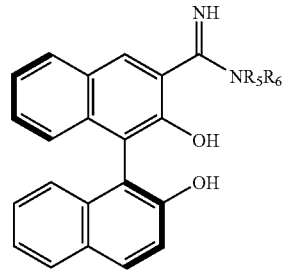
(VII)

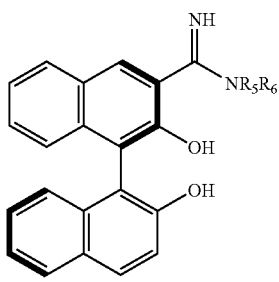

wherein $R_5$ and $R_6$ may be the same or different and each represents a hydrogen atom, a linear or branched alkyl group having 1 to 6 carbon atoms, a linear or branched alkenyl group having 2 to 6 carbon atoms, or an aralkyl group having 7 or 8 carbon atoms, or a salt thereof.

(5) A process for producing a compound represented by the following formula (I) or (II):

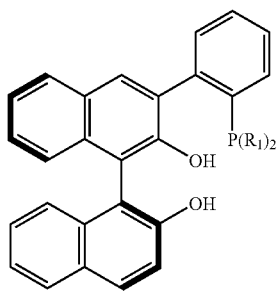

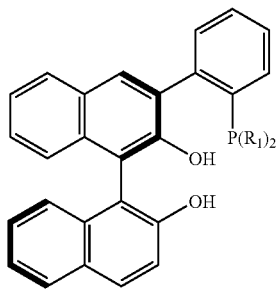

wherein $R_1$ represents a phenyl group which may be substituted by a lower alkyl group or a halogen atom, comprising the following steps of (a) to (e):

(a) a step of reacting a compound of the following formula (IX) or (X):

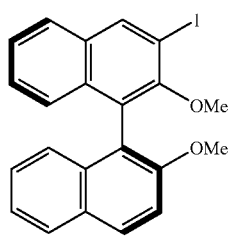

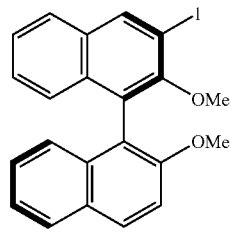

with boronic acid pinacol ester in the presence of a base and an organometallic catalyst, (b) a step of introducing a leaving group into a free phenolic hydroxyl group by reacting the compound obtained in (a) with a sulfonyl chloride or a sulfonic anhydride in the presence of a base, (c) a step of reacting the compound obtained in (b) with a phosphorus reagent represented by $(R_1)_2PO$, in which $R_1$ has the same meaning as defined in the above, in the presence of a base and an organometallic catalyst, (d) a step of removing a protective group in the naphthol of the compound obtained in (c), and (e) a step of reducing a phosphino group of the compound obtained in (d) with a reducing agent in the presence of a base (6) A Process for Producing a Compound Represented by the Following Formula (XIII) or (XIV):

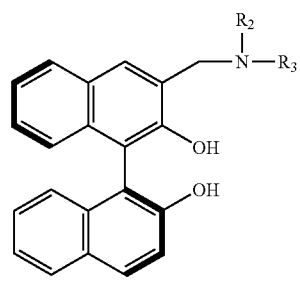

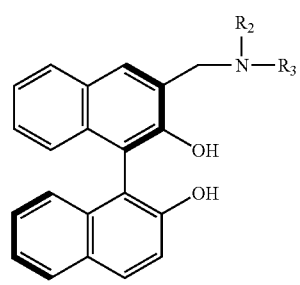

wherein $R_2$ represents a hydrogen atom, a linear or branched alkyl group having 1 to 6 carbon atoms, a linear or branched alkenyl group having 2 to 6 carbon atoms, or an aralkyl group having 7 or 8 carbon atoms, $R_3$ represents a 2-pyridyl group which may be substituted by a lower alkyl group or a halogen atom, a 3-pyridyl group which may be substituted by a lower alkyl group or a halogen atom, or a 4-pyridyl group which may be substituted by a lower alkyl group or a halogen atom, comprising the following steps of (a) and (b):

(a) a step of reacting a compound of the following formula (XI) or (XXI);

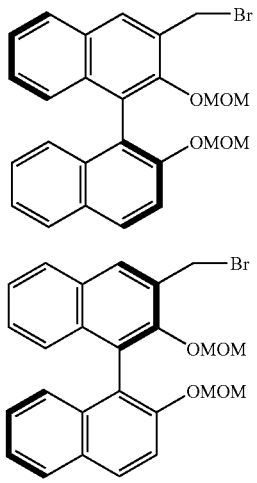

with a (2-, 3-, or 4-)R$_2$NH-pyridine, in which R$_2$ represents the same meaning as defined in the above, in the presence of a base, and (b) a step of removing a protective group in the naphthol of the compound obtained in (a).

(7) A process of carrying out an asymmetric reaction selected from the aza-Baylis-Hillman reaction, the aza-Henry reaction, the Mukaiyama aldol reaction, or a β-lactam-producing reaction using the compound of formula (I) or (II) in (1), the compound of formula (III) or (IV) in (2), the compound of formula (V) or (VI) in (3), or the compound of formula (VII) or (VIII) in (4).

With regard to the technology for producing useful compounds per se, e.g., pharmaceuticals, pesticides, veterinary medicines, functional molecules, and new material compounds, or important synthetic intermediates for producing useful compounds, asymmetric reactions occupy an important position thereof at present. In order to achieve the asymmetric reactions efficiently, a large number of organometallic catalysts have been reported. The inventors of the present invention have found organic molecular catalysts of the above formula (I), (II), (III), (IV), (V), (VI), (VII), or (VIII), which are types containing a phosphorus atom or types containing a pyridine ring, as novel organic molecular catalysts containing no organic metal. Moreover, they have simultaneously succeeded achievement of high asymmetric yields which has not been reported and practical chemical yields by carrying out the aza-Baylis-Hillman reaction using the organic molecular catalysts. By combining the organic molecular catalyst of the above formula (I), (II), (III), (IV), (V), (VI), (VII), or (VIII) provided in the present invention with various asymmetric reactions, it becomes possible to efficiently produce useful compounds per se or important synthetic intermediates for producing useful compounds.

BEST MODE FOR CARRYING OUT THE INVENTION

In the present specification, a lower alky group means an alkyl group having 1 to 4 carbon atoms, such as methyl group, an aralkyl group means a phenylalkyl group, a halogen atom means an iodine atom, a bromine atom, a chlorine atom, or a fluorine atom, and as a halogen which may be present in the group R$_1$ or R$_3$ in formula (I), (II), (III) or (IV), preferably a chlorine atom.

R$_1$ in formula (I) or (II) is preferably an unsubstituted phenyl group.

In formula (III) or (IV), n is preferably 1, R$_2$ is preferably a hydrogen atom, a linear or branched alkyl group having 1 to 6 carbon atoms, or an aralkyl group having 7 or 8 carbon atoms, more preferably a linear or branched alkyl group having 1 to 6 carbon atoms or an aralkyl group having 7 or 8 carbon atoms, and R$_3$ is preferably an unsubstituted 3-pyridyl group.

In formula (VII) or (VIII), R$_5$ and R$_6$ is the same or different and each preferably is a hydrogen atom, a linear or branched alkyl group having 1 to 6 carbon atoms, or an aralkyl group having 7 or 8 carbon atoms, and more preferably one is a hydrogen atom and another is a linear or branched alkyl group having 1 to 6 carbon atoms or an aralkyl group having 7 or 8 carbon atoms.

As reaction conditions for an asymmetric reaction in which the compound of the present invention is used include such as condition wherein the reaction is carried out at −10 to −30° C. for 6 hours to 10 days using 10 mol % of the compound of formula (I), (II), (III), (IV), (V), (VI), (VII), or (VIII) relative to an imine represented by compound (XXIV) or (XXVI) to be described below, and using diethyl ether, tetrahydrofuran, dimethoxyethane, dimethylformamide, methanol, acetonitrile, dichloromethane, chloroform, toluene, cyclopentyl methyl ether and t-butyl methyl ether as reaction solvent. More specifically, in the case of the compound of formula (I) wherein R$_1$ is a phenyl group, reaction conditions include such as condition wherein the reaction is carried out at −20° C. for 6 hours to 10 days in t-butyl methyl ether using 10 mol % of the compound of formula (I) relative to the imine represented by compound (XXIV). Moreover, in the case of the compound of formula (III) wherein R$_2$ is an isopropyl group, R$_3$ is a 3-pyridyl group, and n is 1, reaction conditions include such as condition wherein the reaction is carried out at −15° C. for 0.5 to 10 days in a solvent of cyclopentyl methyl ether:toluene=9:1 using 10 mol % of the compound of formula (III) relative to the imine represented by compound (XXVI).

As the asymmetric reaction carried out using the compound of formula (I), (II), (III), (IV), (V), (VI), (VII), or (VIII), the aza-Baylis-Hillman reaction is preferable.

The salt of the compound of formula (III), (IV), (V), (VI), (VII), or (VIII) include such as hydrochlorides, sulfates, acetates, tetrafluoroborates, trifluoromethanesulfonates, and hexafluorophosphates.

First, the following will describe the production of the optically active phosphinobinaphthol catalyst of formula (I).

Scheme 1

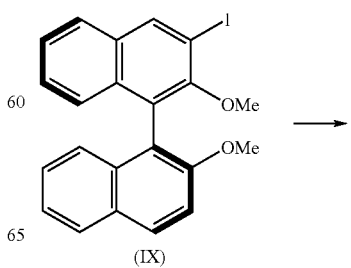

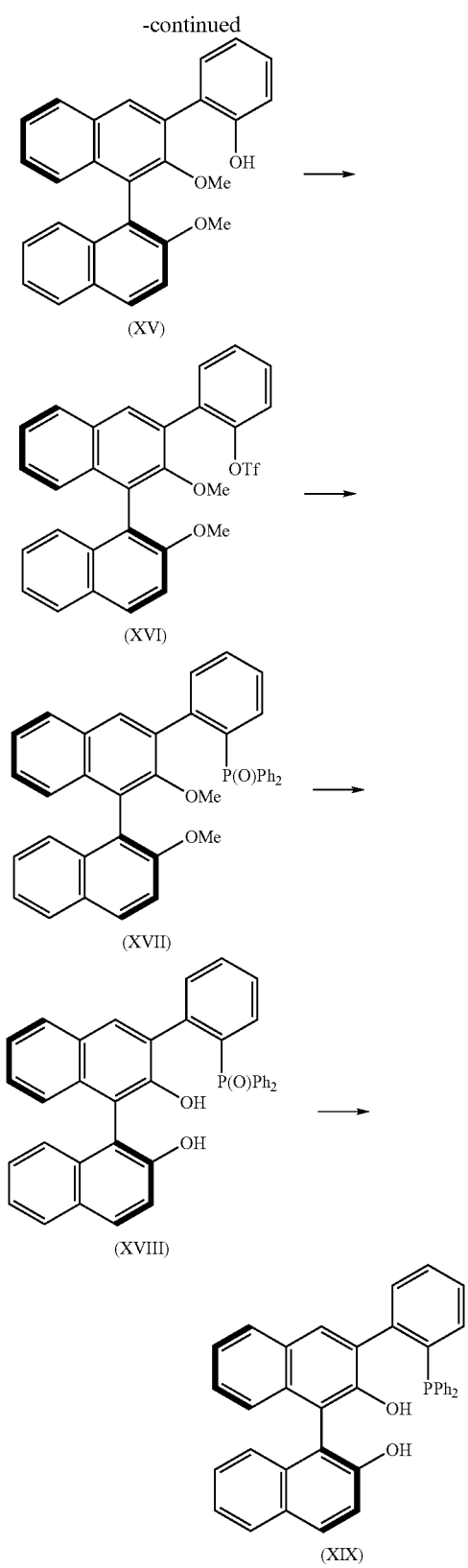

The phosphinobinaphthol catalyst represented by compound (XIX) can be produced using compound (IX) as a starting material by the process described in scheme 1 in which a compound wherein $R_1$ is a phenyl group in formula (I) is described as an example. In scheme 1, Me represents a methyl group and Tf represents a trifluoromethanesulfonyl group.

Firstly, a phenyl group having a hydroxyl group in an o-position is introduced into compound (IX) (*Tetrahedron Lett.*, 37, 4459-4462, 1996) to produce compound (XV). In the production process, using various kinds of compound (IX) or structural analogs thereof, compound (XV) can be produced by utilizing various synthetic reactions for directly combining two benzene rings, such as the Suzuki-Miyaura reaction and the Hiyama reaction. In the case of using compound (IX) as a starting material, an aromatic boron reagent may be suitably used and more specifically, boronic acid pinacol ester may be suitably used. In the production step, the reaction is carried out at 70 to 80° C. with an organic solvent under a basic condition in the presence of an organometallic catalyst. The organometallic catalyst is preferably a palladium catalyst and more preferably, tetrakis(triphenylphosphine)palladium. The base is preferably an inorganic base and more preferably, an aqueous potassium carbonate solution. The organic solvent is preferably an aprotic organic solvent and more preferably, tetrahydrofuran.

Secondly, a phosphorus atom to which one oxygen atom and two phenyl groups are bonded is introduced into the free phenolic hydroxyl group of compound (XV) to produce compound (XVII). The production step usually proceeds in two stages and, for example, compound (XVI) may be a synthetic intermediate through which the step proceeds. At first, a leaving group is first introduced into the phenolic hydroxyl group of compound (XV) under a basic condition to produce compound (XVI). In the production processes, production processes proceeding through synthetic intermediates other than compound (XVI), for example, analogs wherein various leaving groups are introduced and the production processes are also included in the present invention. In the production process of introducing the leaving group, the reaction is achieved by reacting compound (XV) with a reagent for introducing the leaving group at 0 to 25° C. in an organic solvent in the presence of a base. The base is preferably an organic base and more preferably, pyridine. The organic solvent is preferably an aprotic solvent and more preferably, methylene chloride. The reagent for introducing the leaving group is preferably a sulfonyl chloride or a sulfonic anhydride and more preferably, trifluoromethanesulfonic anhydride Then, compound (XVI) is reacted with a substituted phosphorus reagent, e.g., $(R_1)_2PO$, wherein $R_1$ represents the same meaning as defined in the above, to produce compound (XVII). The production step is achieved by reacting compound (XVI) with the substituted phosphorus reagent at 95 to 100° C. in the presence of an organometallic catalyst under a basic condition. The base is preferably an organic base and more preferably, diisopropylamine. The organometallic catalyst is preferably a palladium catalyst and more preferably, palladium acetate. The substituted phosphorus reagent is preferably one of various diarylphosphine oxide. As the reaction solvent, various organic solvents can be used, and the solvent is preferably a high-boiling solvent and more preferably, dimethyl sulfoxide.

Thirdly, two methyl groups which protect the phenolic hydroxyl groups of compound (XVII) are removed to produce compound (XVIII). The production step can be achieved by treating the former compound with a reagent for removing the methyl groups introduced into the phenolic hydroxyl groups, at 0 to 25° C. in an organic solvent. The reaction solvent is preferably methylene chloride=and the reagent for demethylation is preferably a Lewis acid reagent or the like and more preferably, boron tribromide.

Fourthly, the oxygen atom on the phosphorus atom of compound (XVIII) is reduced to produce compound (XIX), which is an objective organic molecular catalyst. The production step is achieved by treating the former compound with a reducing agent at 40 to 50° C. in an organic solvent in the presence of a base. The organic solvent is preferably a hydrocarbon-based organic solvent and more preferably, toluene. The base to be added is preferably an organic base and more preferably, triethylamine. As the reducing agent, a silyl agent such as trichlorosilane is suitably used. Moreover, even when the production step is carried out using a reducing agent other than the silyl reducing agent, the production process is also included in the present invention.

In scheme 1, a methyl group is used as a protective group of the phenolic hydroxyl group in the binol moiety but a process for producing compound (XIX) using a protective group other than the functional group, such as an isopropyl group, a t-butyl group, a methoxymethyl group, a benzyloxymethyl group, a methoxyethoxymethyl group, a 2-(trimethylsilyl)ethoxymethyl group, a methylthiomethyl group, a phenylthiomethyl group, a tetrahydropyranyl group, an allyl group, a cyclohexyl group, a benzyl group, a 4-methoxybenzyl group, or an o-nitrobenzyl group, is also included in the present invention.

As described above, the process for producing compound (XIX) is described according to scheme 1. In the completely same manner as the above production process, an organic molecular catalyst represented by the following formula (XX):

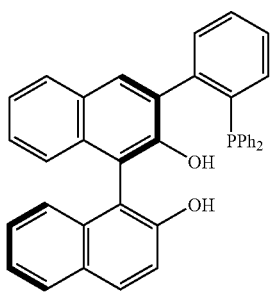

(XX)

can be produced with compound (X) as a starting material and the production process is also included in the present invention.

The following will describe the production of the optically active aminopyridine binaphthol catalyst of formula (XIII).

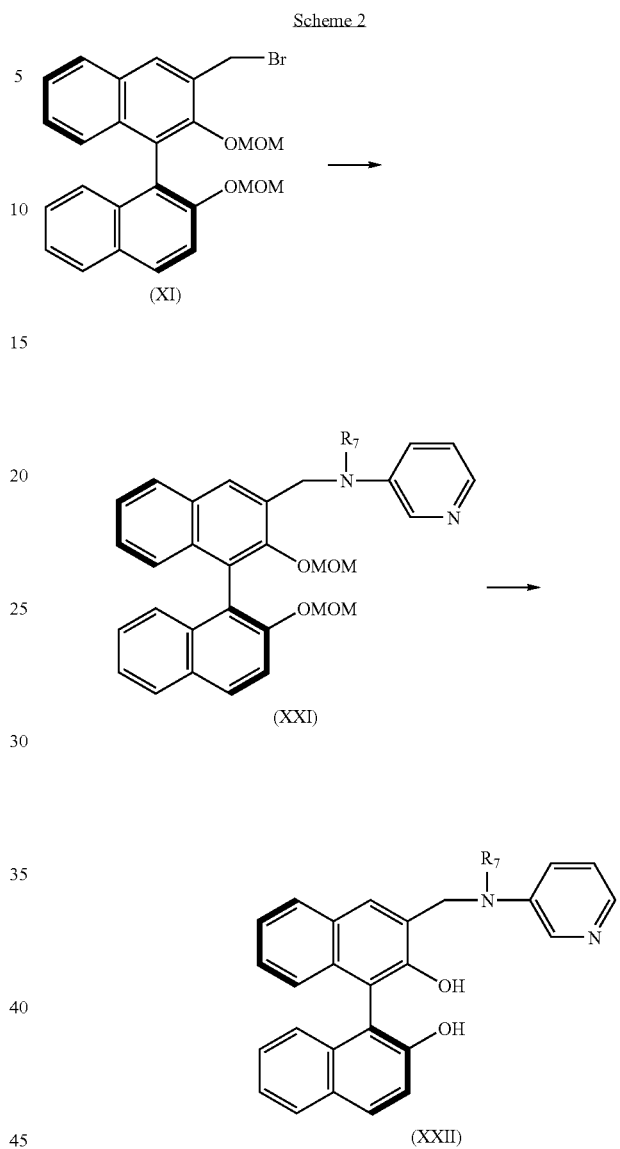

Scheme 2

An aminopyridine binaphthol catalyst of compound (XXII) can be produced with compound (XI) as a starting material by the process described in scheme 2 in which there is described as an example a compound in which, in formula (III), n is 1, $R_2$ is represented as $R_7$ and is a hydrogen atom, an alkyl group having 1 to 6 carbon atoms, an alkenyl group having 2 to 6 carbon atoms, or an aralkyl group having 7 or 8 carbon atoms, and $R_3$ is a 3-pyridyl group which may be substituted. In scheme 2, MOM represents a methoxymethyl group.

At first, compound (XI) is reacted with a 3-alkylaminopyridine (*Tetrahedron Lett.*, 23, 3315-3318, 1982) to produce compound (XXI). The production step is proceeded by treating the former compound with a 3-alkylaminopyridine at 55 to 60° C. in an organic solvent in the presence of a base. The organic solvent is preferably an aprotic solvent and more preferably, tetrahydrofuran. The base is preferably an inorganic base and more preferably, sodium hydride. As the 3-alkylaminopyridine, a wide range of 3-alkylaminopyridines including unsubstituted 3-aminopyridine can be used, i.e., 3-aminopyridine, 3-methylaminopyridine, 3-ethylaminopyridine, 3-isopropylaminopyridine, 3-t-butylaminopyridine, and 3-benzylaminopyridine wherein hydrogen atoms on these pyridine rings may be further substituted by halogens or lower alkyl groups. Preferably, 3-methylaminopyridine, 3-ethylaminopyridine, 3-isopropylaminopyridine, and 3-benzylaminopyridine may be used. A compound wherein the —CH$_2$NR$_7$— moiety in compound (XXI) is —(CH$_2$)$_{2-5}$NR$_7$— can be also produced by using a corresponding halogen derivative, e.g., a compound wherein the CH$_2$Br moiety in formula (XI) is —(CH$_2$)$_{2-5}$Br, other than compound (XI) as a starting material, and the production process is also included in the present invention.

Secondly, the MOM (methoxymethyl) group of compound (XXI) is removed to produce compound (XXII), which is an objective organic molecular catalyst. The production step is achieved by treating the former compound with an acid reagent or the like at 0 to 25° C. in an organic solvent. The organic solvent is preferably a methylene chloride. As the acid catalyst, various inorganic acids and organic acids can be used and more preferably, bromotrimethylsilane is suitably used. With regard to the removal of the MOM group in the step, production processes using various reagents can be devised and these processes are also included in the present invention.

A compound wherein, in formula (III), R$_z$ represents a hydrogen atom, an alkyl group having 1 to 6 carbon atoms, an alkenyl group having 2 to 6 carbon atoms, or an aralkyl group having 7 or 8 carbon atoms and R$_3$ represents a 2-pyridyl group which may be substituted or 4-pyridyl group which may be substituted can be similarly produced by using a corresponding aminopyridine ((2- or 4-)R$_2$NH-pyridine wherein R$_2$ represents a hydrogen atom, an alkyl group having 1 to 6 carbon atoms, an alkenyl group having 2 to 6 carbon atoms, or an aralkyl group having 7 or 8 carbon atoms) instead of the 3-alkylaminopyridine.

In scheme 2, a MOM group is used as a protective group of the phenolic hydroxyl group in the binaphthol moiety, and a process for producing compound (XXII) using a protective group other than the functional group, such as an isopropyl group, a t-butyl group, a methoxymethyl group, a benzyloxymethyl group, a methoxyethoxymethyl group, a 2-(trimethylsilyl)ethoxymethyl group, a methylthiomethyl group, a phenylthiomethyl group, a tetrahydropyranyl group, an allyl group, a cyclohexyl group, a benzyl group, a 4-methoxybenzyl group, or an o-nitrobenzyl group, is also included in the present invention.

As described above, the process for producing compound (XXII) is described according to scheme 2. In the completely same manner as the above production process, an organic molecular catalyst represented by the following formula (XXIII):

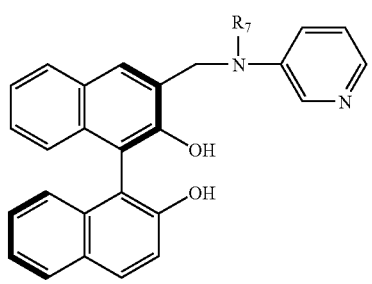

(XXIII)

can be produced starting with compound (XII) as a starting material and the production process is also included in the present invention.

The following will describe useful asymmetric reactions using the organic molecular catalysts invented here. Actually, when the aza-Baylis-Hillman reaction, the aza-Henry reaction, the Mukaiyama aldol reaction, or a β-lactam-producing reaction, or the like which comprises forming a carbon-carbon bond is carried out using the organic molecular catalyst, it was confirmed that high asymmetric yields and practical chemical yields which have not been reported are achieved simultaneously. Therefore, asymmetric catalyst of the present invention can be used for the reactions described above.

The following will describe excellent results in the case when the organic molecular catalysts developed by the present invention are used in the aza-Baylis-Hillman reaction. Detailed results are described in Examples of the present specification.

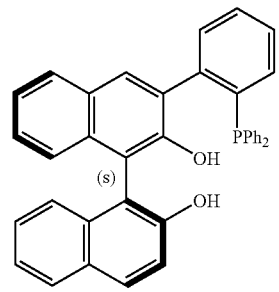

(XIX)

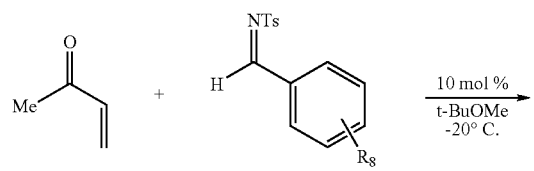

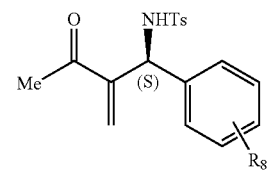

At first, using the optically active phosphinobinaphthol organic molecular catalyst developed in the present invention, i.e., compound (XIX), the aza-Baylis-Hillman reaction shown in the above reaction formula was carried out. As a result, Examples in which high asymmetric yields of 90% or more and practical chemical yields of 90% or more were simultaneously achieved were confirmed in several combinations. Namely, usefulness of the asymmetric aza-Baylis-Hillman reaction using compound (XIX) was proved.

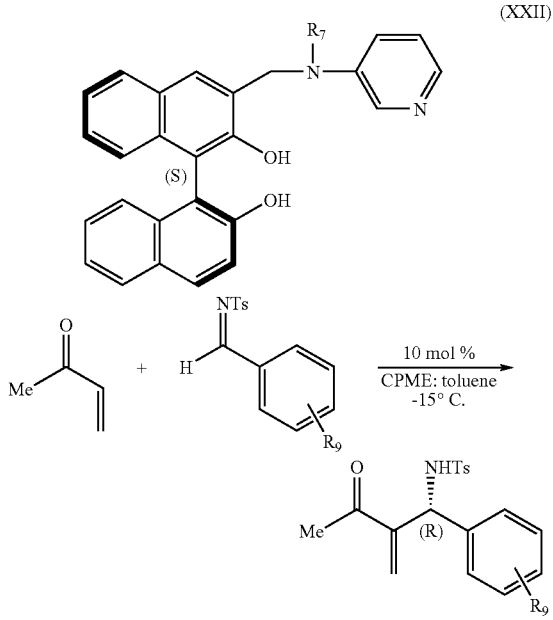

Next, by using the optically active aminopyridine binaphthol organic molecular catalyst developed in the present invention, namely, compound (XXII), the aza-Baylis-Hillman reaction shown in the above reaction formula was carried out. As a result, Examples in which high asymmetric yields of 90% or more and practical chemical yields of 90% or more were simultaneously achieved were confirmed in several combinations. Namely, usefulness of the asymmetric aza-Baylis-Hillman reaction using compound (XXII) was proved.

EXAMPLES

The following will describe the present invention with reference to Examples.

Example 1

Production of Compound (XV)

To a THF (6 ml) solution of a known compound (IX) (*Tetrahedron Lett.*, 37, 4459, 1996) (0.3 mmol) and boronic acid pinacol ester (0.36 mmol), a 1M aqueous $K_2CO_3$ solution (3 ml) and $Pd(PPh_3)_4$ (0.015 mmol) were added, followed by 12 hours of heating under refluxing. After the completion of the reaction, the whole was cooled with ice to room temperature and extracted with methylene chloride (20 ml). The extract liquid was washed with water (5 ml) and a saturated saline (5 ml) and dried over sodium sulfate, and then the solvent was removed by evaporation under reduced pressure. The residue was purified by column chromatography (KANTO silica gel 60N, n-Hex/AcOEt=4/1) to obtain compound (XV) as an orange solid.

$^1$H-NMR (CDCl$_3$): δ 8.02 (1H, d, J=9.2 Hz), 8.00 (1H, s), 7.93 (1H, d, J=8.6 Hz), 7.89 (1H, d, J=8.6 Hz), 7.59 (1H, d, J=7.8 Hz), 7.46 (1H, dt, J=8.6 and 1.3 Hz), 7.41-7.17 (8H, m), 7.08 (1H, d, J=8.9 Hz), 3.82 (3H, s), 3.24 (3H, s)

Example 2

Production of Compound (XVI)

To a methylene chloride solution (3 ml) of compound (XV) (0.3 mmol), pyridine (0.9 mmol) and trifluoromethanesulfonic anhydride (0.6 mmol) were added at 0° C., and the whole was gradually warmed to room temperature and stirred. After the reaction was terminated with water, the whole was extracted with methylene chloride (20 ml) The extract liquid was washed with water (5 ml) and a saturated saline (5 ml) and dried over sodium sulfate, and then the solvent was removed by evaporation under reduced pressure. The residue was purified by column chromatography (KANTO silica gel 60N, n-Hex/AcOEt=4/1) to obtain compound (XVI) as an orange solid.

$^1$H-NMR (CDCl$_3$): δ 7.99 (1H, d, J=9.2 Hz), 7.93 (1H, s), 7.90 (1H, d, J=8.6 Hz), 7.85 (1H, d, J=7.3 Hz), 7.69-7.65 (1H, m), 7.48-7.16 (9H, m), 3.80 (3H, s), 3.06 (3H, s)

Example 3

Production of Compound (XVII)

To a DMSO (6 ml) solution of compound (XVI) (0.3 mmol), diphenylphosphine oxide (0.6 mmol), 1,4-bis(diphenylphosphino)butane (hereinafter abbreviated as DPPB) (0.03 mmol), Pd(OAc)$_2$(0.015 mmol), and diisopropylamine (1.2 mmol) was added, followed by 12 hours of stirring at 100° C. After the completion of the reaction, the whole was warmed to room temperature and the reaction was terminated with water, followed by extraction with ethyl acetate (20 ml). The extract liquid was washed with water (5 ml) and a saturated saline (5 ml) and dried over sodium sulfate. Then the solvent was removed by evaporation under reduced pressure. The residue was purified by column chromatography (KANTO silica gel 60N, n-Hex/AcOEt=4/1) to obtain compound (XVII) as a colorless solid.

$^1$H-NMR (CDCl$_3$): δ 7.96 (1H, d, J=9.2 Hz), 7.75 (1H, s), 7.85-7.04 (21H, m), 7.54 (1H, d, J=7.5 Hz), 6.99 (1H, d, J=8.1 Hz), 3.78 (3H, s), 2.99 (3H, s)

Example 4

Production of Compound (XVIII)

To a methylene chloride solution (3 ml) of compound (XVII) (0.3 mmol), BBr$_3$ (0.9 mmol, 1M methylene chloride solution) was added at 0° C., followed by stirring for 30 minutes. After terminating the reaction with water, the whole was extracted with methylene chloride (20 ml). The extract liquid was washed with water (5 ml) and a saturated saline (5 ml) and dried over sodium sulfate, and then the solvent was removed by evaporation under reduced pressure. The residue was purified by column chromatography (KANTO silica gel 60N, n-Hex/AcOEt=4/1) to obtain compound (XVIII) as a colorless solid.

$^1$H-NMR (CDCl$_3$): δ 7.89 (1H, d, J=8.9 Hz), 7.84 (1H, d, J=7.8 Hz), 7.80-6.98 (23H, m)

Example 5

Production of Compound (XIX)

To a toluene solution (6.7 ml) of compound (XVIII) (0.2 mol), triethylamine (2 mmol) and trichlorosilane were added at 0° C., followed by stirring at 50° C. for 12 hours. After returning the temperature to room temperature and terminating the reaction with a saturated aqueous sodium hydrogen carbonate solution, the whole was filtered through celite and the celite was washed with ethyl acetate. Thereafter, the mother liquid was extracted with ethyl acetate (20 ml). The extract liquid was washed with water (5 ml) and a saturated saline (5 ml) and dried over sodium sulfate. Then the solvent was removed by evaporation under reduced pressure. The residue was purified by column chromatography (KANTO silica gel 60N, n-Hex/AcOEt=4/1) to obtain compound (XIX) as a colorless solid.

$^1$H-NMR (CDCl$_3$): δ 7.96 (1H, d, J=9.2 Hz), 7.88 (1H, d, J=7.3 Hz), 7.80-6.98 (23H, m), 5.18 (2H, brs)

Examples 6 and 7

Production of Compound (XXI)

To THF suspension (0.3 ml) of sodium hydride, a THF (0.7 ml) solution of known $^3$-methylaminopyridine (*Tetrahedron Lett.*, 23, 3315-3318, 1982) (0.24 mmol) or 3-isopropylaminopyridine (JP-A-11-035562 (Japanese patent Application No. 9-192116)) (0.24 mmol) was added at 0° C. The whole was stirred at 60° C. for 2 hours and then the temperature was returned to room temperature. THF solution(1.0 ml) of known compound (XI) (0.2 mmol) (*Tetrahedron Lett.*, 39, 7917-7920, 1998) was added thereto, followed by stirring for 15 minutes After cooling to 0° C. and terminating the reaction with a saturated aqueous ammonium chloride solution, the whole was extracted with methylene chloride (20 ml). The extract liquid was washed with water (5 ml) and a saturated saline (5 ml) and dried over sodium sulfate. Then the solvent was removed by evaporation under reduced pressure. The residue was purified by column chromatography (KANTO silica gel 60N, CH$_2$Cl$_2$/MeOH=9/1) to obtain compound (XXI) as a yellow oil.

Example 6

A Compound wherein R$_7$ is a Methyl Group in Compound (XXI)

$^1$H-NMR (CDCl$_3$): δ 8.25 (1H, d, J=3.0 Hz), 7.99 (2H, d, J=9.2 Hz), 7.89 (1H, d, J=8.6 Hz), 7.75 (1H, d, J=8.1 Hz), 7.61 (1H, s), 7.60 (1H, d, J=8.4 Hz), 7.41-7.11 (6H, m), 7.19 (2H, d, J=7.0 Hz), 5.16 (1H, d, J=7.3 Hz), 5.06 (1H, d, J=7.3 Hz), 4.91 (2H, s), 4.67 (1H, d, J=5.9 Hz), 4.50 (1H, d, J=5.9 Hz), 3.28 (3H, s), 3.18 (3H, s), 3.10 (3H, s)

Example 7

A Compound wherein R$_7$ is an Isopropyl Group in Compound (XXI)

$^1$H-NMR (CDCl$_3$): δ 8.27 (1H, brs), 7.99 (2H, d, J=8.9 Hz), 7.89 (1H, d, J=8.1 Hz), 7.75 (1H, d, J=5.7 Hz), 7.74 (1H, s), 7.60 (1H, d, J=8.4 Hz), 7.41-7.05 (8H, m), 5.15 (1H, d, J=7.0 Hz), 5.07 (1H, d, J=7.0 Hz), 4.74 (2H, s), 4.70 (1H, d, J=5.7 Hz), 4.53 (1H, d, J=5.7 Hz), 4.48-4.36(1H, m), 3.18 (3H, s), 3.12 (3H, s), 1.33 (3H, d, J=6.7 Hz), 1.32 (3H, d, J=6.7 Hz)

Examples 8 and 9

Production of Compound (XXII)

To a methylene chloride solution (1 ml) of compound (XXI) (0.2 mmol), bromotrimethylsilane (0.8 mmol) was added at 0° C., followed by stirring for 30 minutes. After quenching the reaction with water, the whole was extracted with methylene chloride (20 ml). The extract liquid was washed with water (5 ml) and a saturated saline (5 ml) and dried over sodium sulfate. Then the solvent was removed by evaporation under reduced pressure. The residue was purified by column chromatography (KANTO silica gel 60N, CH$_2$Cl$_2$/MeOH=9/1) to obtain compound (XXII) as a yellow solid.

Example 8

A Compound wherein R$_7$ is a Methyl Group in Compound (XXII)

$^1$H-NMR (CDCl$_3$): δ 8.28-8.18 (1H, br), 7.96 (2H, d, J=9.2 Hz), 7.89 (2H, d, J=8.4 Hz), 7.79 (1H, d, J=8.1 Hz), 7.70 (1H, s), 7.39 (1H, d, J=8.9 Hz), 7.34-7.13 (7H, m), 4.76 (2H, s), 3.18 (3H, s)

Example 9

A Compound wherein R$_7$ is an Isopropyl Group in Compound (XXII)

$^1$H-NMR (CDCl$_3$): δ 8.29 (1H, d, J=3.0 Hz), 8.05 (1H, dd, J=4.6 and 1.4 Hz), 7.92 (1H, d, J 8.9 Hz), 7.85 (1H, d, J=7.6 Hz), 7.79-7.65 (2H, m), 7.34 (1H, d, J=7.0 Hz), 7.34-7.19 (5H, m), 7.13 (1H, d, J=5.1 Hz), 7.10 (1H, d, J=8.4 Hz), 7.01 (1H, d, J=8.6 Hz), 4.62 (2H, s), 4.12-3.99 (1H, m), 1.25 (3H, d, J=8.1 Hz), 1.21 (3H, d, J=8.1 Hz)

Examples 10 to 23

The aza-Baylis-Hillman Reaction using Organic Molecular Catalyst Compound (XIX)

Examples 10 to 23 were carried out as described in reaction formula 1 wherein R$_8$ represents a hydrogen atom, a halogen atom, a nitro group, a C$_{1-6}$ alkoxy group, a cyano group, or a C$_{1-6}$ alkyl group and Ts represents a toluenesulfonyl group. Namely, imine (0.05 mmol) represented by compound (XXIV) was added to a t-BuOMe (1 ml) solution of compound (XIX) (0.005 mmol) and the whole was cooled to −20° C. Methyl vinyl ketone (0.15 mmol) was added thereto and the whole was stirred with monitoring the reaction by TLC until the completion of the reaction. After the completion of the reaction, the reaction liquid was purified by column chromatography (KANTO silica gel 60N, n-Hex/AcOEt=2/1) without the post-treatment of the reaction liquid to obtain aza-Baylis-Hillman reaction product compound (XXV). The product was identified by comparing NMR of the product with that of a literature (*Angew. Chem. Int. Ed.*, 41, 4507-4510, 2002).

Reaction formula 1

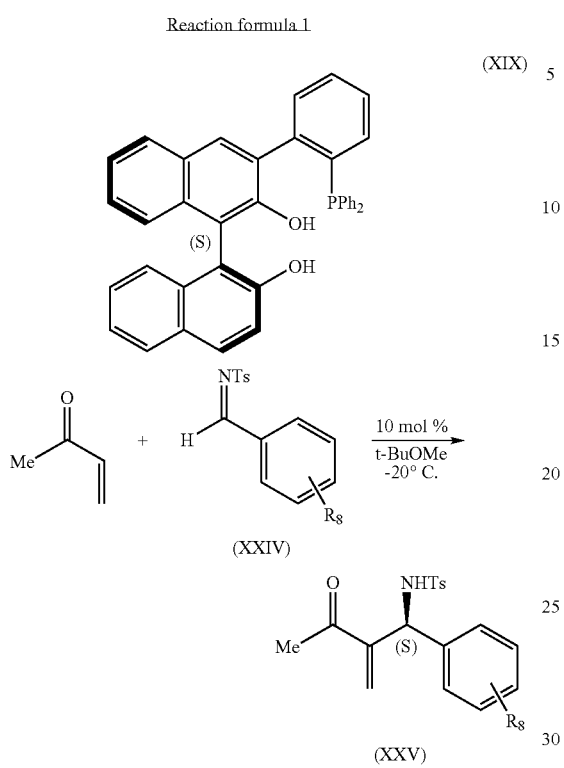

Example 10

The Case when $R_8$ was a Hydrogen Atom

The reaction time was 9 days. The chemical yield was 97%. The asymmetric yield was 87% ee.

Example 11

The Case when $R_8$ was a Fluorine Atom and was Substituted in a p-Position

The reaction time was 7 days. The chemical yield was more than 99t. The asymmetric yield was 89% ee.

Example 12

The Case when $R_8$ was a Chlorine Atom and was Substituted in a p-Position

The reaction time was 6 days. The chemical yield was 90%. The asymmetric yield was 92% ee.

Example 13

The Case when $R_8$ was a Bromine Atom and was Substituted in a p-Position

The reaction time was 4 days. The chemical yield was 87%. The asymmetric yield was 92% ee.

Example 14

The Case when $R_8$ was a Nitro Group and was Substituted in a p-Position

The reaction time was 2 days. The chemical yield was 95%. The asymimetric yield was 82% ee.

Example 15

The Case when $R_8$ was a Nitro Group and was Substituted in a p-Position and the Reaction Temperature was −40° C.

The reaction time was 4 days. The chemical yield was 93%. The asymmetric yield was 88% ee.

Example 16

The case when $R_8$ was a Methoxy Group and was Substituted in a p-Position

The reaction time was 9 days. The chemical yield was 90%. The asymmetric yield was 95% ee.

Example 17

The Case when $R_8$ was a Cyano Group and was Substituted in a p-Position

The reaction time was 6 days. The chemical yield was 90%. The asymmetric yield was 78% ee.

Example 18

The Case when $R_8$ was a Methyl Group and was Substituted in a p-Position

The reaction time was 10 days. The chemical yield was 91%. The asymmetric yield was 89% ee.

Example 19

The Case when $R_8$ was an Ethyl Group and was Substituted in a p-Position

The reaction time was 8 days. The chemical yield was more than 99%. The asymmetric yield was 93% ee.

Example 20

The Case when $R_8$ was a Chlorine Atom and was Substituted in a m-Position

The reaction time was 7 days. The chemical yield was 87%. The asymmetric yield was 77% ee.

Example 21

The Case when $R_8$ was a Nitro Group and was Substituted in a m-Position

The reaction time was 3 days. The chemical yield was more than 99%. The asymmetric yield was 62% ee.

Example 22

The Case when $R_8$ was a Nitro Group and was Substituted in a m-Position and the Reaction Temperature was −40° C.

The reaction time was 6 days. The chemical yield was 92%. The asymmetric yield was 73% ee.

Example 23

The Case when $R_8$ was a Chlorine Atom and was Substituted in an o-Position The reaction time was 6 days. The chemical yield was 96%. The asymmetric yield was 92% ee.

Examples 24 to 29

The aza-Baylis-Hillman Reaction using Organic Molecular Catalyst Compound (XXII)

Examples 24 to 29 were carried out as described in reaction formula 2 wherein $R_7$ represents the same meaning as described above and Ts represents a toluenesulfonyl group. Namely, imine (0.05 mmol) was added to a CPME (cyclopentylmethyl ether):toluene (9:1, 0.5 ml) solution of compound (XXII) (0.005 mmol) and then methyl vinyl ketone (0.15 mmol) was added thereto at −15° C. The whole was stirred with monitoring the reaction by TLC until the reaction was completed. After the completion of the reaction, the reaction liquid was purified by column chromatography (KANTO silica gel 60N, n-Hex/AcOEt=2/1) without the post-treatment of the reaction liquid to obtain an aza-Baylis-Hillman reaction product.

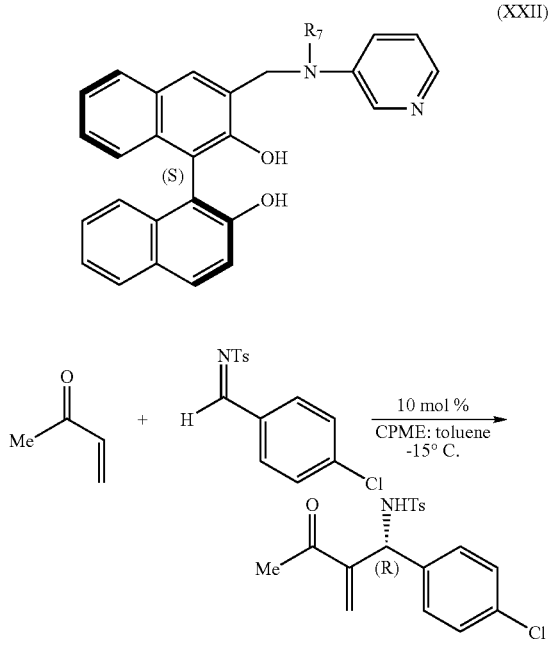

Reaction formula 2

Example 24

The Case when $R_7$ was a Hydrogen Atom

The reaction time was 10 days. The chemical yield was 62%. The asymmetric yield was 87% ee.

Example 25

The Case when $R_7$ was a Methyl Group

The reaction time was 6 days. The chemical yield was 97% The asymmetric yield was 90% ee.

Example 26

The Case when $R_7$ was an Ethyl Group

The reaction time was 5.5 days. The chemical yield was 90%. The asymmetric yield was 91% ee.

Example 27

The Case when $R_7$ was an Isopropyl Group

The reaction time was 2 days. The chemical yield was 95%. The asymmetric yield was 94% ee.

Example 28

The Case when $R_7$ was a t-Butyl Group

The reaction time was 10 days. The chemical yield was 72. The asymmetric yield was 83% ee.

Example 29

The Case when $R_7$ was a Benzyl Group

The reaction time was 6 days. The chemical yield was more than 99%. The asymmetric yield was 93% ee.

Examples 30 to 47

The aza-Baylis-Hillman Reaction using Organic Molecular Catalyst which is Compound (XXII) wherein $R_7$ is an Isopropyl Group Examples 30 to 47 were carried out as described in reaction formula 3 wherein $R_{10}$ represents a hydrogen atom, a methyl group, an ethyl group, or a phenyl group, $R_{11}$ represents a phenyl group, a naphthyl group, or a furyl group which may be substituted by a hydrogen atom, a halogen atom, a nitro group, a $C_{1-6}$ alkoxy group, a cyano group, or a $C_{1-6}$ alkyl group, and Ts represents a toluenesulfonyl group. Namely, imine (0.05 mmol) represented by compound (XXVI) was added to a CPME (cyclopentylmethyl ether):toluene (9:1, 0.1 ml) solution of compound (XXII) (0.005 mmol) wherein $R_7$ is an isopropyl group and then methyl vinyl ketone (0.15 mmol) was added thereto at −15° C. The whole was stirred with monitoring the reaction by TLC until the reaction was completed. After the completion of the reaction, the reaction liquid was purified by column chromatography (KANTO silica gel 60N, n-Hex/AcOEt=2/1) without the post-treatment of the reaction liquid to obtain aza-Baylis-Hillman reaction product compound (XXVII).

The product was identified by comparing NMR of the product with that of a literature (*Angew. Chem. Int. Ed.*, 41, 4507-4510, 2002).

Reaction formula 3

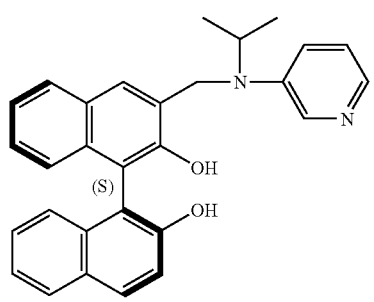

Example 30

The Case when $R_{10}$ was a Methyl Group and $R_{11}$ was a Phenyl Group

The reaction time was 7 days. The chemical yield was 93%. The asymmetric yield was 87% ee.

Example 31

The Case when $R_{10}$ was a Methyl Group and $R_{11}$ was a p-Fluorophenyl Group The reaction time was 3 days. The chemical yield was 95%. The asymmetric yield was 93% ee.

Example 32

The Case when $R_{10}$ was a Methyl Group and $R_{11}$ was a p-Chlorophenyl Group The reaction time was 2.5 days. The chemical yield was 96%. The asymmetric yield was 95% ee.

Example 33

The Case when $R_{10}$ was a Methyl Group and $R_{11}$ was a p-Bromophenyl Group The reaction time was 1.5 days. The chemical yield was 93%. The asymmetric yield was 94% ee.

Example 34

The Case when $R_{10}$ was a Methyl Group and $R_{11}$ was a p-Nitrophenyl Group The reaction time was 0.5 days. The chemical yield was 91%. The asymmetric yield was 91% ee.

Example 35

The Case when $R_{10}$ was a Methyl Group and $R_{11}$ was a p-Methoxyphenyl Group The reaction time was 5.5 days. The chemical yield was 93%. The asymmetric yield was 94% ee.

Example 36

The Case when $R_{10}$ was a methyl group and $R_{11}$ was a p-Cyanophenyl Group The reaction time was 2.5 days. The chemical yield was more than 99%. The asymmetric yield was 91% ee.

Example 37

The Case when $R_{10}$ was a methyl group and $R_{11}$ was a p-Methylphenyl Group The reaction time was 8 days. The chemical yield was 90%. The asymmetric yield was 90% ee.

Example 38

The Case when $R_{10}$ was a Methyl Group and $R_{11}$ was a p-Ethylphenyl Group The reaction time was 5 days. The chemical yield was 97%. The asymmetric yield was 93% ee.

Example 39

The Case when $R_{10}$ was a Methyl Group and $R_{11}$ was a m-Chlorophenyl Group The reaction time was 3 days. The chemical yield was 93%. The asymmetric yield was 93% ee.

Example 40

The Case when $R_{10}$ was a Methyl Group and $R_{11}$ was a m-Nitrophenyl Group The reaction time was 1 day. The chemical yield was 94%. The asymmetric yield was 86% ee.

Example 41

The Case when $R_{10}$ was a Methyl Group and $R_{11}$ was an o-Chlorophenyl Group The reaction time was 3.5 days. The chemical yield was 92%. The asymmetric yield was 62% ee.

Example 42

The Case when $R_{10}$ was a Methyl Group and $R_{11}$ was an α-Naphthyl Group The reaction time was 12 days. The chemical yield was 88%. The asymmetric yield was 70% ee.

Example 43

The Case when $R_{10}$ was a Methyl Group and $R_{11}$ was a β-Naphthyl Group The reaction time was 4.5 days. The chemical yield was 95%. The asymmetric yield was 91% ee.

Example 44

The Case when $R_{10}$ was a Methyl Group and $R_{11}$ was a 2-Furyl Group

The reaction time was 2 days. The chemical yield was more than 99%. The asymmetric yield was 88% ee.

Example 45

The Case when $R_{10}$ was a Hydrogen Atom and $R_{11}$ was a p-Nitrophenyl Group The reaction time was 1.5 days. The chemical yield was 95%. The asymmetric yield was 94% ee.

Example 46

The Case when $R_{10}$ was an Ethyl Group and $R_{11}$ was a p-Nitrophenyl Group The reaction time was 4 days. The chemical yield was 87%. The asymmetric yield was 88% ee.

Example 47

The Case when $R_{10}$ was a Phenyl Group and $R_{11}$ was a p-Nitrophenyl Group The reaction time was 8 days. The chemical yield was 91%. The asymmetric yield was 58% ee.

This application is based on Japanese applications No. 2004-204183 filed on Jul. 12, 2004, the entire contents of which are incorporated hereinto by reference.

While the invention has been described in detail and with reference to specific embodiments thereof, it will be apparent to one skill in the art that various changes and modifications can be made therein without departing from the spirit and scope thereof. All references cited herein are incorporated, by reference, in their entirety.

What is claimed is:

1. A compound represented by formula (III) or (IV):

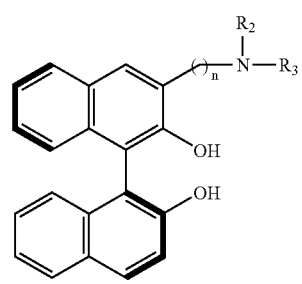

(III)

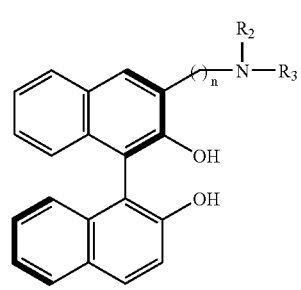

(IV)

wherein n represents an integer of from 1 to 6, $R_2$ represents a hydrogen atom, a linear or branched alkyl group having from 1 to 6 carbon atoms, a linear or branched alkenyl group having from 2 to 6 carbon atoms, or an aralkyl group having 7 or 8 carbon atoms, $R_3$ represents a 2-pyridyl group which may be substituted by a lower alkyl group or a halogen atom, a 3-pyridyl group which may be substituted by a lower alkyl group or a halogen atom, or a 4-pyridyl group which may be substituted by a lower alkyl group or a halogen atom, or a salt thereof.

2. A process for producing a compound of formula (XIII) or (XIV):

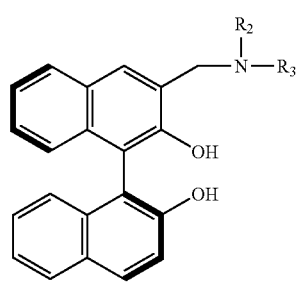

(XIII)

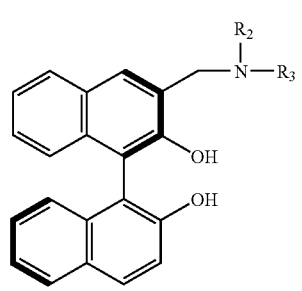

(XIV)

wherein $R_2$ represents a hydrogen atom, a linear or branched alkyl group having from 1 to 6 carbon atoms, a linear or branched alkenyl group having from 2 to 6 carbon atoms, or an aralkyl group having 7 or 8 carbon atoms, $R_3$ represents a 2-pyridyl group which may be substituted by a lower alkyl group or a halogen atom, a 3-pyridyl group which may be substituted by a lower alkyl group or a halogen atom, or a 4-pyridyl group which may be substituted by a lower alkyl group or a halogen atom;

wherein the process comprises (a) reacting, in the presence of a base, a compound of formula (XI) or (XII):

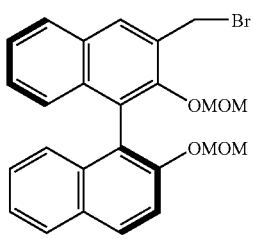
(XI)

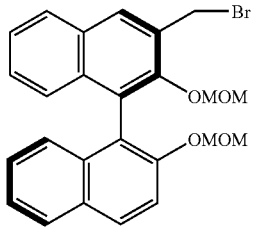
(XII)

wherein MOM represents a protective group, with a (2-, 3-, or 4-)$R_2$NH-pyridine wherein $R_2$ has the same meanings as above, and (b) removing the protective groups on the protected binaphthol compound obtained in (a).

3. The process of claim 2, wherein MOM represents an isopropyl group, a t-butyl group, a methoxymethyl group, a benzyloxymethyl group, a methoxyethoxymethyl group, a 2-(trimethylsilyl)ethoxymethyl group, a methyithiomethyl group, a phenyithiomethyl group, a tetrahydropyranyl group, an allyl group, a cyclohexyl group, a benzyl group, a 4-methoxybenzyl group, or an o-nitrobenzyl group.

4. The process of claim 2, wherein MOM represents a methoxymethyl group.

* * * * *